March 15, 1955 W. KORDES Plant Pat. 1,363
ROSE PLANT
Filed June 14, 1954
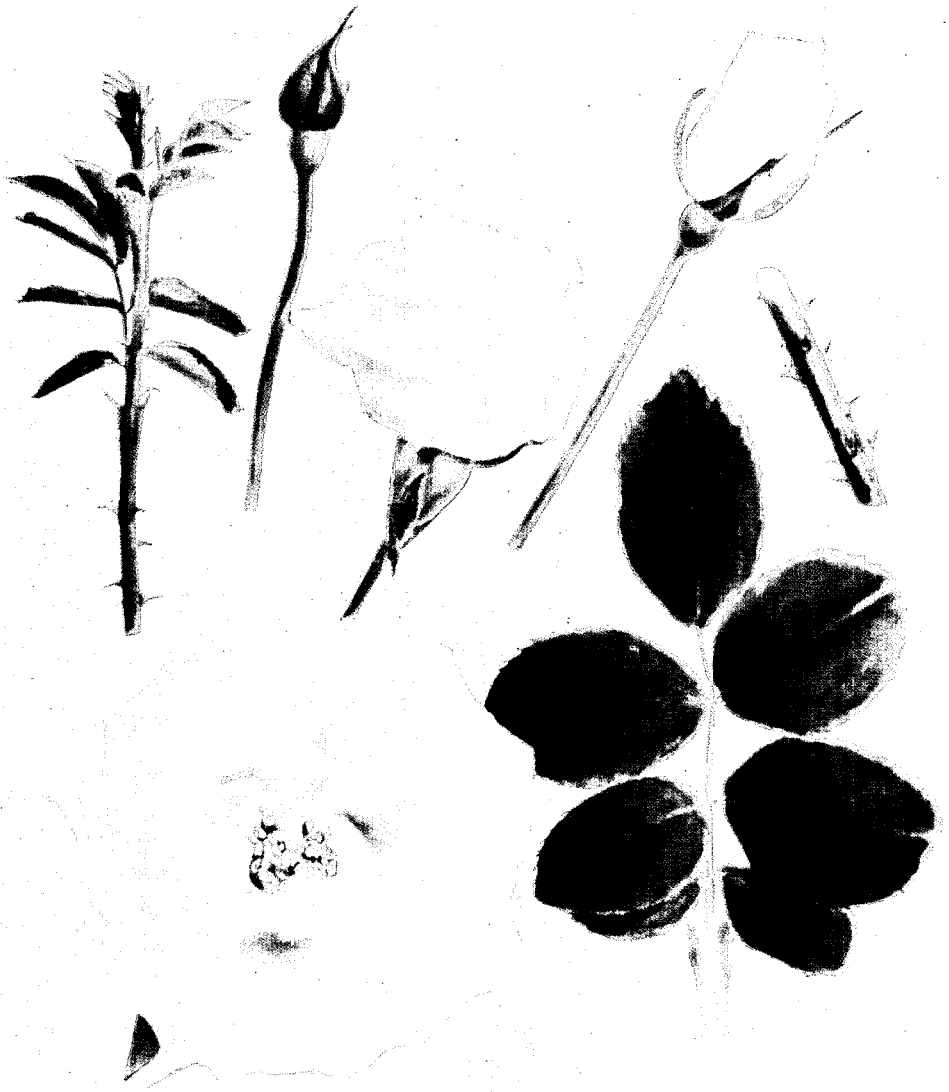
Inventor.
Wilhelm Kordes
By: Robb & Robb
Attorneys.

United States Patent Office

Plant Pat. 1,363

Patented Mar. 15, 1955

1,363

ROSE PLANT

Wilhelm Kordes, Bei Elmshorn, Holstein, Sparrieshoop, Germany, assignor to Jackson & Perkins Company, Newark, N. Y., a corporation of New York Application June 14, 1954, Serial No. 436,754

1 Claim. (Cl. 47—61)

The present invention relates to a new and distinct variety of rose plant of the large-flowered polyantha class, which was originated by me by crossing the variety "Independence" (Plant Patent No. 1036) with the variety "Crimson King" (unpatented).

The primary objective in making this cross was to obtain a new variety which bears hybrid tea size flowers in a brilliant color like those of the variety "Independence." This objective was fully achieved, as evidenced by the fact that my new variety bears large cupped flowers, the general color tonality of which is Spectrum Red, lightly overcast with Scarlet Red in the half-open flower, which changes to Scarlet Red, lightly overcast with Rose Red in the fully open flower.

In addition to the foregoing features, my new variety is further characterized by the vigorous habit of growth of the plant. Together, these features represent a unique and desirable combination in a rose of this class, and definitely distinguish my new variety from its parents, as well as from all other varieties of which I am aware.

Asexual reproduction of my new variety by budding at Newark, New York, U. S. A., and also at Pleasanton, California, U. S. A., shows that the foregoing characteristics and distinctions come true to form and are established and transmitted through succeeding propagations.

The accompanying drawing shows typical specimens of the flowers, stems and foliage of my new variety in different stages of development and depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Independence."
*Pollen parent.*—"Crimson King."
Classification:
*Botanic.*—Large-flowered polyantha.
*Commercial.*—Floribunda.

FLOWER (Observations made from specimens grown outdoors at Newark, New York, U. S. A., in the latter part of the month of June, and about mid-morning.)

Blooming habit: Recurrent—continuous.
Bud:
*Size.*—Large.
*Form.*—Urn-shaped; is not affected by wet or hot weather.
*Color.*—When sepals first divide—Carmine, Plate 1. When petals begin to unfurl—Spectrum Red, Plate 1. When half blown: inside of petals—Spectrum Red, Plate 1, lightly overcast with Scarlet Red, Plate 1; reverse of petals—Rose Red, Plate 12, lightly overcast with Pomegranate Purple, Plate 12.
*Sepals.*—Serrated; slightly branched; curl back when petals begin to unfurl. Color: inside—Absinthe Green, Plate 31; outside—Bice Green, Plate 17.
*Calyx.*—Color—Biscay Green, Plate 17. Shape—pear. Size—small. Aspect—smooth. Odor when rubbed—none.
*Peduncle.*—Length — medium. Aspect — smooth. Strength—erect; slender. Color—Spinach Green, Plate 5.

*Opening.*—Opens up well; is not affected by adverse weather conditions.
Bloom:
*Size.*—Large. Average size when fully expanded—4½ inches.
*Borne.*—Singly and several together.
*Stems.*—Medium length; strong.
*Form (when first open).*—Cupped. Permanence—retains its form to the end, but outer petals curl back.
*Petalage.*—Double (full but open center). Number of petals under normal conditions—20 to 25.
*Color.*—Center of flower—Scarlet Red, Plate 1, lightly overcast with Begonia Rose, Plate 1. Outer petals—Begonia Rose, Plate 1, lightly overcast with Rose Red, Plate 12. Base of petals (aiglet)—Glass Green, Plate 31. Inside of petals—Scarlet Red, Plate 1, lightly overcast with Rose Red, Plate 12. Reverse of petals—Rose Red, Plate 12, lightly overcast with Spinel Pink, Plate 26. General tonality from a distance—Scarlet Red, Plate 1.
*Discoloration.*—General tonality at end of first day—Scarlet Red, Plate 1. Second day—Scarlet Red, Plate 1, lightly overcast with Begonia Rose, Plate 1. Third day—Scarlet Red, Plate 1, lightly overcast with Rose Red, Plate 12.
Petals:
*Texture.*—Leathery; is not affected by wet or hot weather.
*Appearance.*—Inside—velvety. Outside—satiny.
*Form.*—Oval.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

GENITAL ORGANS

Stamens, anthers: Large; few, regularly arranged around styles. Color—Capucine Yellow, Plate 3.
Stamens, filaments (threads): Long. Color—Spinel Red, Plate 26.
Pollen: Color—Light Buff, Plate 15.
Styles: Columnar; uneven length; medium length; thin.
Stigmas: Color—Primrose Yellow, Plate 30.
Ovaries: All enclosed in calyx.
Hips: None.
Seeds: None.

PLANT

Form: Bush.
Growth: Vigorous; bushy.
Foliage: 5 to 7 leaflets.
*Size.*—Large.
*Quantity.*—Abundant.
*Color.*—New foliage: upper side—Yellowish Oil Green, Plate 5, overcast with Neutral Red, Plate 38; under side—Oxblood Red, Plate 1. Old Foliage: upper side—Cedar Green, Plate 6, lightly overcast with Garnet Brown, Plate 1; under side—Light Cress Green, Plate 31.
*Shape.*—Oval.
*Texture.*—Upper side—leathery. Under side—smooth.
*Ribs and veins.*—Ordinary.
*Edge.*—Serrated (saw-toothed).
*Serration.*—Single; small.
*Leaf stem.*—Color—Lumiere Green, Plate 17. Under side—prickles.
*Stipules.*—Long; serrated.
Wood:
*New wood.*—Color—Oil Green, Plate 5. Bark—smooth.
*Old wood.*—Color—Light Bice Green, Plate 17. Bark—smooth.
Thorns:
*Thorns.*—Quantity: on main stalks from base—many; on laterals from stalk—many. Form—narrow base; medium length; some straight and some hooked downward. Color (when young)—Spinel Red, Plate 26. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the vigorous habit of growth of the plant, and the distinctive brilliant color of its cupped flowers which have a general color tonality of Spectrum Red lightly overcast with Scarlet Red in the half-open flower, changing to Scarlet Red lightly overcast with Rose Red in the fully open flower.

No references cited.